United States Patent [19]
Grodberg

[11] Patent Number: 5,286,490
[45] Date of Patent: Feb. 15, 1994

[54] TRANSDERMAL FLUORIDE MEDICATION

[75] Inventor: Marcus G. Grodberg, Newton, Mass.

[73] Assignee: Colgate-Palmolive Company, Piscataway, N.J.

[21] Appl. No.: 518,905

[22] Filed: May 4, 1990

[51] Int. Cl.$^5$ .................. A61F 13/02; A61L 15/16; A61K 9/14; A01N 59/10

[52] U.S. Cl. .................................. 424/448; 424/449; 424/484; 424/486; 424/673; 424/676; 514/946; 514/947; 514/955; 514/964

[58] Field of Search ............... 424/448, 449, 484, 486, 424/601, 673, 676; 514/946, 947, 955, 964

[56] References Cited

FOREIGN PATENT DOCUMENTS 0181970 5/1986 European Pat. Off. ............ 424/449
9006736 6/1990 World Int. Prop. O. .......... 424/448

*Primary Examiner*—Thurman K. Page
*Assistant Examiner*—Carlos Azpuru
*Attorney, Agent, or Firm*—Paul Shapiro; Robert C. Sullivan

[57] ABSTRACT

A transdermal fluoride medication for providing fluoride ion for the prevention and treatment of bone loss disease, which may have an estrogen-containing substance for not only treating hormonal imbalance but to obtain more advantageous use of the fluoride ion within the body. A transdermal enhancer is present. The preferred form is a transdermal patch containing sodium monofluorophosphate and further optionally including an estrogen-containing substance and a transdermal enhancer, which is adhesively attached on the skin of the patient for slow release of fluoride ion and, optionally, estrogen to the bloodstream of the patient. Up to ten percent of sodium fluoride and/or calcium can be added.

10 Claims, No Drawings

TRANSDERMAL FLUORIDE MEDICATION

BACKGROUND OF THE INVENTION

1. Field of the Invention

This invention relates to transdermal medication fluoride drug product for treatment or prevention of osteoporosis or other bone disease. More particularly, this invention relates to the use of sodium monofluorophosphate, alone or in combination with another fluorine compound, and, optionally, with an estrogen-containing substance and, if desired, a calcium containing substance, in a transdermal patch suitable for use in the treatment and prevention of osteoporosis, alveolar bone loss or other bone diseases where systemic fluoride ion is efficacious and further treating hormonal imbalance and enhancing utilization of the fluoride ion by introduction of estrogen.

2. Description of the Prior Art

Fluoride stimulates the activity of bone-forming cells and, together with calcium and phosphate, the two major mineral components of bone is also stored in the bone structure. Fluoride seems to directly stimulate the proliferation of osteoblasts resulting in an increase in bone formation.

U.S. Pat. No. 3,287,219 discloses the oral administration of sodium fluoride to promote bone healing.

The role of fluoride in strengthening the teeth and in imparting acid resistance and preventing caries in dental treatment is well documented. The use of sodium fluoride tablets and liquids for infants and young children in areas where the drinking water is not or is only insufficiently fluoridated is well known. For this purpose, fluoride ion from NaF is administered in dosages of about 0.25 to about 1 mg per day. Representative patents in this area include U.S. Pat. Nos. 3,306,824, 4,265,877 and 4,397,837 (toothpaste). The use of sodium monofluorophosphate (MFP) in dental products, particularly toothpaste products, as an anticaries fluoride additive is also well known and is mentioned in U.S. Pat. No. 4,397,837, cited above. The MFP is slowly metabolized by an intestinal enzyme, MFPase or alkaline phosphatase into free fluoride ion which, in turn, is absorbed into the blood stream, some of the MFP being directly absorbed in the liver and converted therein to F ion.

More recently, the use of NaF or MFP for the treatment of bone disease to promote bone formation and strengthen bone has received wide attention. In fact, although not yet approved for use in the United States, both NaF and MFP products for the treatment and prevention of osteoporosis are available in Europe. Thus, Flurexal ® is an enteric coated tablet containing 22 mg sodium fluoride (10 mgF) sold by Zyma SA Nylon Suisse; Tridin ® is a chewable tablet containing 38 mg sodium monofluorophosphate (5 mg F), 500 mg calcium gluconate monohydrate, 500 mg calcium citrate tetrahydrate, 200 mg carboxymethyl cellulose, available from Opfermann Arzneimittel GmbH.

According to the directions for use provided with the medications, Flurexal ® should be taken three times each day, while Tridin ® should be taken one to two tablets three times a day for treatment or one tablet three times a day for prevention of steriod-osteoporosis. In general, the typical recommended dosage for F ion is in the order of from about 20 to 50 mg per day for a human adult.

The literature provided with Tridin ® states that gastric and intestinal irritation is seldom observed. To the same effect, Yngve Ericsson, "Monofluorophosphate Physiology: General Considerations," Caries Res. 17 (Suppl. 1), pages 46–55 (1983), reported that "neither in patients nor in numerous experiments with laboratory workers has any subjective discomfort been recorded with doses up to 30 mg F as MFP." However, in one of the present inventors' own clinical studies and patient evaluations, the occurrence of gastric and intestinal distress was observed in a significant number of cases.

Attempts to solve the adverse side effects of gastrointestinal (GI) tract symptoms by minimizing the availability of F ion in the stomach by providing NaF in a sustained release form have only been partially effective in avoiding GI irritation. More particularly, it has been observed that, while slow release sodium fluoride is well tolerated by approximately 70% of patients, there is adverse gastrointestinal effects in the other approximate 30% of patients.

The use of MFP in slow release form is described in recently issued U.S. Pat. Nos. 4,859,467 and 4,861,590. Transdermal patches have become well known for dosage of medications, such as nitroglycerin for treatment of angina, scopolamine for treatment of motion sickness and numerous others. To this end, various transdermal enhancers have been used for facilitating the delivery of the medication through the skin of the user.

SUMMARY OF THE INVENTION

The present invention relates to a transdermal patch for application of a fluoride medication and, optionally, of estrogen to the patient with or without calcium and/or phosphate-containing substances. To this end, on a thin fluid impervious bottom sheet, a base sheet for strengthening the patch is bonded. The periphery of the bottom sheet opposite the base sheet may be coated with a pressure-sensitive adhesive or adhesion may be attained from the medication, which includes one or more fluoride containing substances and, optionally, estrogen, calcium and phosphate-containing substances, as well as a transdermal enhancer.

DETAILED DESCRIPTION OF THE INVENTION

Osteoporosis can be broadly defined as increasing weakness and fragility of the bones. It most frequently occurs in elderly, post-menopausal women and in elderly (presenile or senile) men, but also occurs in idiophathic forms. Osteoporosis can also occur in connection with, i.e. as an undesirable side effect of, corticoid treatment (steriod-osteoporosis). Certain localized forms of bone disease may also be associated with a general weakness and fragility of the bone structure due to insufficient new bone formation. Therapeutic indications includes any bone wasting disease, genetic, such as osteogenesis imperfecta, or acquired, such as renal bone disease.

In women undergoing menopause and post-menopausal females there is often present an hormonal imbalance heretofore treated by oral dosages of estrogen or by injection of estrogen.

One of the effects of advanced periodontal disease is the loss of alveolar bone (i.e. that portion of the jaw bones that support the teeth) mass, which eventually causes loosening and loss of teeth. Alveolar bone loss may also occur after tooth extractions and, in some cases, after the insertion of dental implants.

Bone is composed of an organic phase, collagen and an inorganic crystalline phase of calcium phosphate, or more specifically, hydroxyapatite, $Ca_{10}(PO_4)_6(OH)_2$. Fluoride plays an important role in the prevention of bone loss by stimulating the formation of less soluble fluorapatite $Ca_{10}(PO_4)_6F_2$. Therefore, in osteoporosis, alveolar bone loss and other bone diseases associated with general weakening or loss of the bone tissue, or in cases where the normal dietary intake of calcium is insufficient, a dietary supplement to supply additional calcium is usually appropriate. The addition to the calcium supplement of, or the separate administration of, a source of fluoride ion will, according to recent scientific research, greatly enhance the reversal of bone loss, the fluoride stimulating new bone formation and the calcium being an indispensable building block for bone tissue.

Sodium fluoride and sodium monofluorophosphate can each be used to provide the fluoride ion to be absorbed into the blood for eventual skeletal uptake. Sodium fluoride, NaF, has the advantage that it has a higher F content than sodium monofluorophosphate, MFP. NaF is also more rapidly absorbed, at least in the first few hours, into the blood. However, NaF has higher acute toxicity than MFP and causes stomach irritation in a much higher percentage of patients than does MFP. Moreover, and perhaps most important, is the fact that NaF is incompatible with ionizable calcium compounds, forming poorly soluble $CaF_2$, thereby depleting the availability of the F ion to a large extent and of the Ca ion to a smaller extent (based on the much greater total quantity of calcium present in the patient's system). On the other hand, MFP is compatible with ionizable calcium compounds since Ca(MFP) is about twenty times more soluble than $CaF_2$.

Unfortunately, when ingested orally in the recommended dosages, typically about 20 to 50 mg F per day for human adults, MFP, although not as pronounced as NaF, also causes stomach irritation.

In accordance with the present invention, it has been found that by incorporating the MFP alone or in combination with a small amount of sodium fluoride, the occurrence of GI irritation can be avoided when using the transdermal patch according to the present invention.

According to the present invention, a transdermal patch is employed which employs a bottom thin plastic sheet of, for example, polyethylene or polypropylene overlying which is a strengthening base sheet bonded at its periphery to the bottom sheet. Suitable base sheets include particularly those of a non-woven hydrophobic fiber, such as nylon, which is substantially non-tearable. Other hydrophobic fibers, such as polyethylene or polypropylene fibers, can be employed which are effective in strengthening the transdermal patch though not as strong as a heat bonded non-woven nylon.

The patch is preferably circular in shape and is formed by stamping simultaneously under heated conditions the bottom and base sheets to bond the peripheries of the two sheets together. This is accomplished by the suitable application of heat during stamping.

The bottom sheet on the side not bonded to the base sheet along the peripheral edges of the patch is coated with a pressure-sensitive adhesive to ensure at least initial attachment of the transdermal patch to the skin of the wearer. When the patch is to be applied to the thighs of the patient, the patches are preferably round in configuration. Such circular shape is the most efficient because of presenting less likelihood of peeling as would occur if sharper curvatures were used, as in oval shaped or corners to be found in other geometrical shapes.

The medication to be applied by the patch includes monofluorophosphate with or without castor oil or glycerine and any of the well-known transdermal enhancers such as N-dodecyl pyrrolidone, N-tetradecyl pyrrolidone (and corresponding caprolactams), as well as longer chain substituted dioxolanes and dioxanes.

Preferably, the transdermal enhancer to be used is N-dodecyl pyrrolidone. In addition to the monofluorophosphate, from five to twenty percent, preferably five to ten percent, of NaF by weight, compared to the amount of monofluorophosphate, may be employed.

A calcium containing substance, as well as a phosphate containing substance, may be employed, as well as an estrogen containing substance.

In use the transdermal patch is employed by application on the skin of the patient in a location as prescribed by the physician.

Typical formulations for use in a transdermal patch according to the invention are shown immediately below:

EXAMPLE 1

| Ingredient | Amount (milligrams) |
| --- | --- |
| Monofluorophosphate | 200.0 |
| Transdermal enhancer | 100.0 |
| Total | Content weight 300.0 mg |

The transdermal enhancer is preferably N-dodecyl pyrrolidone for all Examples.

EXAMPLE 2

| Ingredient | Amount (milligrams) |
| --- | --- |
| Sodium monofluorophosphate | 200.0 |
| Conjugated Estrogens USP | .5 |
| Castor Oil | 5.0 |
| Transdermal enhancer | 94.5 |
| Total | Content weight 300.0 mg |

The amount of conjugated estrogens USP may vary from 0.3 to 0.625 mg. The transdermal enhancer with the monofluorophosphate produces an adhesive-like composition with the castor oil.

EXAMPLE 3

In lieu of conjugated estrogens USP, esterified estrogens USP in an amount varying from 0.2 to 0.4 mg may be employed, preferably 0.3 mg. As a result, not only is hormonal imbalance treated, but the estrogen has the additional effect of enhancing utilization of the fluoride ion.

EXAMPLE 4

In lieu of the conjugated estrogens USP in Example 2, there is utilized estradiol and derivatives USP in an amount varying from 0.02 to 0.2 mg, preferably 0.1 mg. As a result, not only is hormonal imbalance treated, but the estrogen has the additional effect of enhancing utilization of the fluoride ion.

These formulations provide F ion and estrogen and are designed to release the fluoride ion and estrogen in the bloodstream slowly.

The use of sodium monofluorophosphate as the sole fluoride source is preferred. However, if desired, the formulations can include small amounts of NaF or other fluoride compound. Thus, NaF in amounts from five to ten percent, up to twenty percent, by weight based on the total weight of NaF+MFP can be added.

In addition to each of the above Examples, other active ingredients may be included which are as follows:

Calcitriol, (1,25-Dihydroxyvitamin $D_3$ form.
Phosphates, Potassium and Sodium Mono- and Dibasic Phosphates.

The transdermal patch is packaged individually in a fluid proof package after a peelable fluid proof cover sheet of larger size than the patch is applied overlying the medication.

What is claimed is:

1. A transdermal medication comprising a patch including a fluid proof bottom sheet, carrying a pharmaceutically acceptable salt of monofluorophosphate and a transdermal enhancer.

2. A medication according to claim 1, wherein said transdermal enhancer is N-dodecyl pyrrolidone.

3. A medication according to claim 1, including a strengthening base sheet of non-woven hydrophobic fibers overlying said bottom sheet.

4. A medication according to claim 3, wherein said bottom sheet and said base sheet are bonded along their peripheries.

5. A medication according to wherein said bottom sheet and said base sheet are bonded along their peripheries, the periphery of said bottom sheet having a pressure-sensitive adhesive thereon.

6. A medication according to claim 1, wherein said bottom sheet is circular in shape.

7. A transdermal medication according to claim 1 including selected amounts of an estrogen-containing substance.

8. A medication according to claim 1,1 including from five to ten percent by weight of sodium fluoride as compared to the amount of monofluorophosphate.

9. A transdermal medication patch comprising a bottom sheet of a fluid impervious material, a strengthening base sheet bonded to said bottom sheet, and a medication containing a fluoride ion emitting substance and a transdermal enhancer.

10. A patch according to claim 9, wherein said patch is circular in shape and has a coating of a pressure-sensitive adhesive around the periphery of said bottom sheet.

* * * * *